United States Patent [19]

Kuck

[11] 4,226,534
[45] Oct. 7, 1980

[54] MICROPOLARIMETER

[75] Inventor: Julius A. Kuck, Cos Cob, Conn.

[73] Assignee: Fairfield University, Fairfield, Conn.

[21] Appl. No.: 959,885

[22] Filed: Nov. 13, 1978

[51] Int. Cl.³ .................... G01N 21/03; G01N 21/21; G01N 21/23

[52] U.S. Cl. .................................. 356/367; 356/246; 356/440

[58] Field of Search .............................. 356/364–370, 356/440, 246; 350/14–15, 81, 170; 250/225; 422/102, 104

[56] References Cited

U.S. PATENT DOCUMENTS 3,141,094  7/1964  Strickler .............................. 356/440

FOREIGN PATENT DOCUMENTS 501330 12/1921 France ..................................... 356/368

OTHER PUBLICATIONS

Hallmond, A. F., "Manual of the Polarizing Microscope", Cooke, Troughton & Simms, Ltd., 1953, pp. 72–79.

*Primary Examiner*—John K. Corbin
*Assistant Examiner*—Wm. H. Punter
*Attorney, Agent, or Firm*—Robert Ames Norton

[57] ABSTRACT

The micropolarizing equipment of the present invention consists in a pair of capillary tubes of black glass or glass with a black outer coating which fit into sockets in three prisms, the first being a 45° prism over the central aperture of the microscope stage which reflects the plane polarized beam at right angles through one of the capillary tubes; a second prism, which is double, reflects light emerging from the first capillary tube at right angles up to a second 45° prism into which the second capillary tube is mounted in a socket and is parallel to the first capillary tube. The third prism receives the other end of the second capillary tube in a socket and reflects the light up into the objective of the microscope. While split field, null point determination may be used, a much more efficient device is one or more small anisotropic crystals mounted, for example in a drop of liquid or in a thin film, on the top of the third prism and located to be in the path of the light reflected up into the objective of the microscope. The crystal, or one of the crystals, when viewed with polarizer and analyzer crossed is bright, usually in color depending on the wavelength of the light source used, and the particular crystal on which the microscope objective is focused disappears when the stage has been turned to compensate for the optical rotation of the sample in the two capillaries. The extinction of the crystal is very sharp and is preferred over split field devices.

5 Claims, 2 Drawing Figures

MICROPOLARIMETER

BACKGROUND OF THE INVENTION

The polarizing microscope itself is a well known device, and while it is necessary in the combination of the present invention, it is not the novel element. No modification of the microscope is needed except, as will appear below, for supporting clips which are mounted on pillars considerably longer than the conventional microscope slide clips and preferably using a rotatable analyzer which can be mounted over the eyepiece.

The micropolarimeter tubes of the present invention are capillaries in black glass or glass with the outside painted in a non-reflecting black. The use of capillaries in black glass as such is known but in an ordinary type of polarimeter in which the polarized light passes through a capillary tube parallel to the axis of the tube and after passing through an analyzer a null point is determined by the conventional split field, which forms a null point when the two fields are of the same brightness as the polarimeter tube is turned to compensate for the optical rotation of the material in the capillary. The use of black glass capillaries is described, for example, in the publication "Die Arbeitsmethoden der Mikrochemie," by Julius Donau, the description appearing on pages 62 to 64.

The micropolarimeters which have been described require long capillary tubes of the customary length and means for rotating the tubes and for determining when the rotation has compensated for the optical rotation of the material in the tube. These relatively long black capillary tubes present problems of very precise alignment since the lumen of the capillary is so small and filling of the capillary is extremely difficult in a long tube because of possible defects in the tube and the necessity of avoiding small air bubbles. Every time a new sample is measured, the apparatus has to be disassembled, the tube filled, and the instrument reassembled.

In spite of the disadvantages referred to above, micropolarimetry has been used, and if sufficient care is taken, reasonable accuracy is obtained. Of course, the capillary tube has the enormous advantage of using minute quantities of a sample to be measured. This varies from a fraction of a drop for 0.5 mm. capillaries to about three drops for a 2.0 mm. capillary. Needless to say, these minute quantities are an order of magnitude or more less than the amounts which are required for an ordinary sized polarimeter tube.

SUMMARY OF THE INVENTION

The present invention is a combination of elements most of which are individually known optical elements. Thus a polarizing microscope is used with a rotating stage and can be of any conventional design. On the stage there is placed an assembly of three prisms and two much shorter capillary tubes, also of black glass or with non-reflecting black paint on the outside, as has been described in the preceding section of this specification. The two capillary tubes mount in precisely aligned and sized sockets in three prisms. The first prism is a 45° prism which turns plane polarized light coming up through the conventional central aperture of the polarizing microscope stage through 90°, passing through the first capillary, which is parallel to the plane of the microscope stage. The other end of the capillary mounts in a precise socket in a second prism, which is formed of two 45° prism sections. While, as stated above, there are three elements, actually, because there are two 45° prismatic elements, functionally there are four 90° reflections.

The second black glass capillary tube receives light from the second element of the prism which then passes through the second capillary tube, which is above and parallel to the first one, and also parallel to the plane of the microscope stage. The other end of this second tube fits in an accurate socket in the third 45° prism, and light passing through the tube is reflected up at 90° into the objective of the microscope.

The assembly of prisms and capillary tubes may be held together with a clip or even an elastic band around them. However, since the holes in the prisms are quite accurately bored, there is a sufficient friction fit so that it is, at least theoretically, possible to omit any clip holding the elements of the two tubes and the prisms together. Preferably, a clip, elastic band, or some other means for holding the assembly of the two capillaries and prisms together is used even though, as pointed out above, the device will operate without any clips. The prisms are held in proper position on the microscope slides by two clips which extend from columns in the microscope stage. These clips are slightly different than in the ordinary polarizing microscope in that they extend from pillars which are higher than those normally used for holding a microscope slide. Pillars, of course, can be exchanged so that the microscope can be used as an ordinary polarizing microscope when it is not being employed as part of a micropolarimeter of the present invention. The longer pillars and clips do not receive any redesign of the microscope, and it is an advantage that standard microscopes can be used.

While it is possible with some additional elements to use a split field device for determining null point of rotation of the polarimeter element, this is more awkward, and the present invention includes in a more specific aspect a greatly improved null point determining element, namely a small anisotropic crystal in a drop of liquid or in a thin film on top of the third prism so that the light passes through the drop into the objective. When the capillaries have been filled with the minute quantity of the sample, the optical rotation of which is to be measured, but before the microscope stage has been rotated to determine the optical rotation of the sample, the crystal, or one of them if there are a number in the drop, which is preferable for convenience although only one crystal is performing, it is quite bright. If the device is used in a preferred manner with light of a particular wavelength, the anisotropic crystal will appear bright and usually also colored, depending on the wavelength of the light source. In order to have the sharpest contrast a rotatable analyzer is slipped over the eyepiece of the microscope. This analyzer is turned until the field is dark and hence the anisotropic crystal is very bright and is usually in color depending on the wavelength of light being used in the microscope. When the rotatable analyzer is operated it does not have to be with extreme precision, it being only necessary to rotate it to the point where the field is dark. The fact that the rotatable analyzer does not have to be precisely adjusted is a practical advantage.

After checking and observing the bright anisotropic crystal, the rotatable stage of the microscope is turned using, if necessary, the vernier, which is present on all polarizing microscope stages. When the rotation exactly compensates for the rotation of polarized light of the sample in the capillaries, the anistropic crystal suddenly disappears. This is an extremely sharp null point, and the rotation of the stage is, of course, read and gives the optical rotation of the sample.

While in the preferred and best form of the present invention small anisotropic crystals are necessary, within limits the smaller the better as a small crystal will give an even sharper null point than a somewhat larger one, the invention is not limited to the use of any particular anisotropic crystal. An example of one is potassium dihydrogen phosphate. Other anisotropic crystals are known and may be used, depending on the particular wavelength of light source employed. Thus with some light sources potassium dihydrogen phosphate is by no means the best anisotropic crystal. It is a simple matter to choose crystals once the light source has been decided upon.

After the polarimetric operation has been completed, the assembly of capillary tubes and prisms is removed by loosening the clips holding them to the stage and can then be disassembled by pulling out the capillaries from their sockets in the prisms, cleaning out the capillaries, and refilling them with a different sample, followed by reassembly in the prisms. The short capillary tubes which are so easily disassembled make changing of samples quite simple but it is sometimes desirable where a large number of different samples is to be examined to have them in already filled capillaries which then only have to be assembled in the holes of the prisms, the whole clipped together or held together, if this is felt desirable; and therefore a number of tests may be made in a very short time, much shorter than in long capillaries in the more conventional polarimeters, which cannot be disassembled or filled as easily and as quickly.

While the polarizing microscope and its accessories are necessary elements in the combination of the present invention, they are not what distinguishes the invention from the prior art. It is the combination of the various elements, and, in the case of the preferred form, the new null point element of the anisotropic crystal, which constitutes the invention. This is common in combination inventions where a number of old elements are used in a new assembly, and that is the case here.

It is an advantage of the present invention that it can be used with any polarizing microscope. In the description of the preferred embodiments which follow in a later section in this specification, a Unitron microscope, made by the Unitron Instrument Company, is illustrated. This is a very satisfactory device but any other polarizing microscope may be used.

The present invention using a polarizing microscope with the capillary tubes and prism arrangement and/or preferred null point determining element is quite compact and lends itself to an extensive degree of portability. Where the device of the present invention is to be used indefinitely in a single laboratory, this portability is, of course, not needed. However, if it is desired to move the polarimeter from one location to another, the compactness of the device is a definite advantage.

It is possible to consider the capillaries and their prisms with, preferably, the anisotropic crystal as an accessory to a polarizing microscope because the microscope does not need any redesign to perform the functions of the present invention, except for the obvious one of longer clip pillars, and preferably means for darkening the field so that the anisotropic crystal forms a bright contrast. As has been stated above, such a means for darkening the field may be, any preferably is, a rotatable polarizer which also can act as an analyzer and which can be slipped over the eyepiece of the microscope. Therefore, in the present invention there is also included the prism and capillary assembly as a sub-combination. It should be understood, of course, that the microscope is necessary to the complete instrument but as the capillary-prism combination, which is the novel portion of the present combination, may be produced and/or sold separate from the microscope, the subcombination as an accessory is included.

DESCRIPTION OF THE PREFERRED EMBODIMENTS

Figure 1:
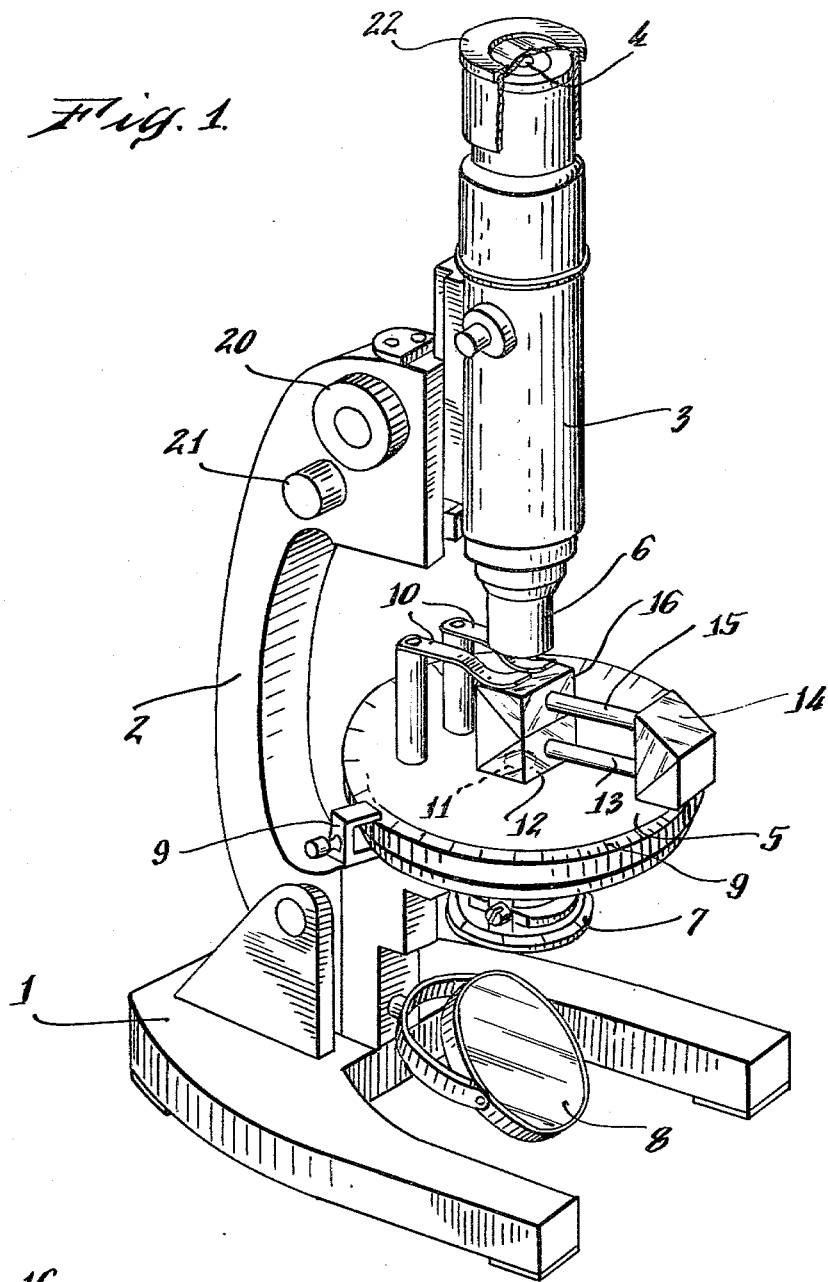
FIG. 1 is a perspective view, partly broken away, of a polarizing microscope with the capillary tube crystal assembly and null point anisotropic crystal.

FIG. 1 shows a microscope made by the Unitron Instrument Company although, as has been stated above, this is only one very suitable microscope which can be used.

The base of the microscope is shown at (1), the support for the microscope barrel proper at (2), and the microscope elements barrel (3), eyepiece (4), and objective (6), and a rotatable analyzer (22) which is slid over the microscope barrel covering the eyepiece. In the drawings this analyzer is shown partly broken away for clarity. Coarse and fine focusing knobs (20) and (21) are mounted on the arm (2), which is conventional.

A light source, (not shown), is reflected by the conventional mirror (8) through a polarizer (7) and up through a central opening (11) in the stage (5). The stage can be rotated and is marked, as usual, and provided with the customary vernier (9).

Figure 2:
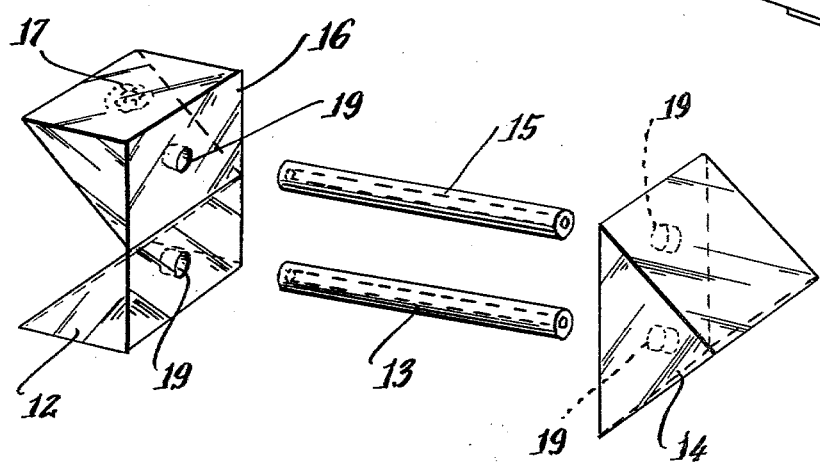
FIG. 2 is an exploded view of the capillary tubes and prisms.

On the microscope stage (5) there is mounted or placed the assembly of capillary tubes and prisms, which is shown in exploded form in FIG. 2. Light passing up through the central aperture (11) of the stage is reflected by the 45° prism (12) through the lower capillary tube (13) which is mounted in a socket (19) in the prism. It will be noted that the other sockets in the prisms will receive the same reference numeral (19) as they are performing the same function. The capillary (13) with its fine lumen, shown in phantom, is made of black glass and can be filled with the minute amount of sample to be tested for optical rotation. The other end of the capillary enters a socket (19) in the double 45° prism (14). This prism reflects the light at right angles, and the second or upper portion of the prism again reflects it at right angles back through the upper capillary tube (15) which fits into the socket (19) in a prism (16). This reflects it up through a drop of liquid or through a thin film containing one or several very small anisotropic crystals, shown at (17), and up into the objective of the microscope. One of the anisotropic crystals is in the direct path of the light and when viewed in maximum darkness between the crossed polarizer and analyzer, after the analyzer (22) has been slipped over the eyepiece of the microscope, is bright and usually colored, depending upon the wavelength of the polarized light striking it. But if the plane of polarization of the light passing up through the crystal is rotated for any reason, either by turning the polarizer or by passing the light through an optically rotating liquid, the analyzer is turned until the field is dark again so that the anisotropic crystal appears very bright by contrast. The darkening of the field is not a critical adjustment. The stage (5) is now rotated using the vernier (9) until the anisotropic crystal disappears.

The assembly of capillaries and prisms are held properly centered as far as prisms (12) and (16) are concerned by the clips (10), which are mounted on conventional pillars as are the usual microscope slide holding clips. Because of the greater thickness of the capillary and prism assembly, the pillars, of course, are much longer than in the case of slides.

If desired, the capillary-prism tube assembly may be held together with a clip or an elastic band, neither of which is shown as they would only confuse the drawing, and as the assembly of capillaries and prisms with the capillaries in their sockets can be used without a clip, that is what is shown in FIG. 1.

After the measurement has been made, as described above, the capillary and prism assembly is removed and, if desired, disassembled and the capillaries filled with a new sample, or other capillaries already filled with the sample as described in connection with the drawings, and the assembly again mounted on the stage of the microscope with the drop of liquid containing the anisotropic crystals (17) on the top of the prism (16). Measurement is then effected as has been described above.

I claim:

1. A micropolarimeter comprising in combination a polarizing microscope provided with a conventional light source, microscope elements, rotating stage, polarizer, and analyzer, and a null point indicator, the microscope being adjusted to pass polarized light through the conventional opening in the stage and up through the microscope proper, a measuring element comprising two short capillary tubes mounted in two 45° prisms and one double 45° prism, the double 45° prism being oriented so that light entering a face is reflected at right angles and again at right angles back through the same face, the prisms having holes in their faces aligned with the hole from the face of the first prism to a hole in the face of the double prism and the second hole in the face of the double prism being aligned with the hole in the second 45° prism, capillary tubes of diameter to fit snugly in the holes and mounted to form an assembly with the capillaries parallel, and parallel to the microscope stage, the prisms being oriented so that the first 45° prism is over the opening in the stage and the second 45° prism is aligned with the microscope, whereby polarized light passes up into the first 45° prism, is reflected at right angles through the first capillary tube, then reflected twice in the double 45° prism and returned through the second capillary tube to the second 45° prism said null point indicating device is an anisotropic crystal mounted in a liquid on the upper face of said second 45 prism in the path of said light from said second capillary tube and reflected by said second 45 prism.

2. A micropolarimeter according to claim 1 in which the capillaries are of black glass.

3. A polarimeter measuring accessory adapted for positioning on the rotatable stage of a polarizing microscope and comprised of a first 45° prism having a flat surface suitable for mounting over the central aperture of the stage of the polarizing microscope and reflecting polarized light at right angles, a capillary tube, the first prism being provided with a hole in its face of a diameter so that the capillary tube fits snugly therein, a double 45° prism, the double prism being provided with a hole in its entrance face of diameter so that the capillary tube fits snugly therein, and reflects received light back through an exit face parallel to the entrance face and provided with a hole, second capillary tube fitted snugly into the second hole and oriented parallel to the first capillary tube, a third 45° prism, said third prism having a hole in its entrance face into which the second capillary fits snugly, the prism being oriented so that reflected light enters the microscope, said third prism having an anisotropic crystal mounted in a liquid on its upper face in the path of light reflected by the prism from the second capillary.

4. An accessory for a polarizing microscope according to claim 3 in which the analyzer is rotatable to produce a dark field for enhancing the contrast of the anisotropic crystal.

5. An accessory for polarizing microscope according to claim 4 in which the capillary tubes are of black glass.

* * * * *